(12) United States Patent
Kodama et al.

(10) Patent No.: US 6,599,749 B1
(45) Date of Patent: Jul. 29, 2003

(54) METHOD OF CONVEYING SAMPLE RACK AND AUTOMATED ANALYZER IN WHICH SAMPLE RACK IS CONVEYED

(75) Inventors: Ryuichiro Kodama, Hitachinaka (JP); Hiroshi Mitsumaki, Mito (JP); Tomonori Mimura, Tomobe-machi (JP); Takayuki Noda, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/389,583

(22) Filed: Sep. 3, 1999

Related U.S. Application Data

(63) Continuation of application No. 08/835,518, filed on Apr. 8, 1997, now Pat. No. 6,117,683.

(30) Foreign Application Priority Data

Apr. 10, 1996 (JP) ............................................... 8-87902

(51) Int. Cl.[7] ............................................... G01N 35/04
(52) U.S. Cl. .......................... 436/47; 436/48; 422/65; 422/67
(58) Field of Search ................ 422/65, 67; 436/47, 436/48

(56) References Cited

U.S. PATENT DOCUMENTS

| | | | |
|---|---|---|---|
| 4,058,367 A | 11/1977 | Gilford | |
| 4,678,755 A | * 7/1987 | Shinohara et al. | ............ 436/43 |
| 5,087,423 A | 2/1992 | Ishibashi | |
| 5,350,564 A | 9/1994 | Mazza et al. | |
| 5,366,896 A | 11/1994 | Margrey et al. | |
| 5,380,488 A | 1/1995 | Wakatake | |
| 5,614,415 A | 3/1997 | Markin | |

FOREIGN PATENT DOCUMENTS

| | | |
|---|---|---|
| EP | 97105800 | 6/1988 |
| JP | 63-217273 | 9/1988 |
| JP | 3-183955 | 8/1991 |
| JP | 4-65670 | 3/1992 |
| JP | 5-26882 | 2/1993 |
| JP | 6-207943 | 7/1994 |
| JP | 7-92171 | 4/1995 |
| JP | 63-271164 | 11/1998 |

* cited by examiner

Primary Examiner—Jan Ludlow
(74) Attorney, Agent, or Firm—Mattingly, Stanger & Malur, P.C.

(57) ABSTRACT

An automated analyzer device has a main conveyance line capable of conveying a sample rack holding a sample, a plurality of analysis units arranged along the main conveyance line, a rack supplying device for supplying the sample rack to the main conveyance line and a rack housing device for housing the sample rack conveyed by the main conveyance line. The automated analyzer includes a controller for confirming that there is no sample rack on the main conveyance line before the main conveyance line receives the sample rack from the rack supplying device. The controller controls operation of the main conveyance line so as to convey the sample rack received from the rack supplying device by the main conveyance line to a position corresponding to a specific one of the plurality of analysis units by which the sample rack is to be received without stopping.

8 Claims, 8 Drawing Sheets

US 6,599,749 B1

METHOD OF CONVEYING SAMPLE RACK AND AUTOMATED ANALYZER IN WHICH SAMPLE RACK IS CONVEYED

This is a continuation application of U.S. Ser. No. 08/835,518, filed Apr. 8, 1997 now U.S. Pat. No. 6,117,683.

BACKGROUND OF THE INVENTION

The present invention relates to an automated analyzer and a method for conveying a sample rack holding a sample to be analyzed, and more particularly, to an automated analyzer and a method for arranging a plurality of analysis units along a main conveyance line and automatically conveying a sample rack via the main conveyance line.

As examples of arranging a plurality of analysis units along a conveyance line and delivering a sample on a sample rack conveyed by the conveyance line to the analysis unit, for example, Japanese Patent Application Laid-Open Nos. 5-26882, 63-271164, and 7-92171 are known.

Among them, an automated multi-item analyzer disclosed in JP-A-5-26882 uses a method of sequentially transferring sample racks to a conveyance line, stopping the sample rack on the conveyance line, and delivering the sample on the sample rack to an analysis unit. An automated analysis system disclosed in JP-A-63-271164 uses a method in which a circulating path is formed by connecting a plurality of belt conveyors via cross-over rollers, a plurality of analysis units are arranged along the circulation path, the sample rack sent from a rack supplying unit is conveyed by the circulation path, the movement is stopped when the sample rack is positioned in front of the analysis unit, and a sample is delivered from the sample rack on the circulation path to the analysis unit. A vessel conveying system disclosed in JP-A-7-92171 uses a method of arranging a plurality of analysis units along a conveyance line, each analysis unit has a sub-line having an identification information reader, the number of vessels according to an analysis processing ability per a predetermined time of each analysis unit are taken in the sub-line, and the vessel is transferred to the conveyance line after the sample is delivered on the sub-line.

According to the conveying method disclosed in JP-A-5-26882, since the sample is delivered while the sample rack is stopped on the conveyance line, even when the delivery work to the subsequent sample rack is finished, the way of the subsequent sample rack is disturbed until the delivery of the sample of the preceding sample rack for a plurality of analysis items is finished. The subsequent sample rack is not conveyed during such a period and has to wait on the conveyance line.

According to the conveying method of JP-A-63-271164, identification information of a sample rack is read by a bar code reader after the conveyance of the sample rack by the circulation path is started, and the sample rack is conveyed to a relevant analysis unit. However, when the relevant analysis unit is performing the delivery work, the sample rack started to be conveyed has to be stopped on the circulation path, so that the conveyance of subsequent sample racks is disturbed.

According to the conveying method of JP-7-92171, a predetermined number of vessels are sent to the sub-line of the analysis unit according to the analysis processing ability of each analysis unit. After a vessel is sent to the sub-line, however, identification information of the vessel is read and whether the vessel is adapted to a test target of the analysis unit or not is determined. When the vessel is not adapted to the analysis unit, it means that the vessel is conveyed to an unnecessary path for the vessel.

SUMMARY OF THE INVENTION

It is, therefore, an object of the invention to provide a method of conveying a sample rack and an automated analyzer in which when a sample rack is conveyed, the way of the sample rack is not disturbed by other sample racks stopped and the sample rack is prevented from being carried in to a path useless for the sample rack, and time required to convey the sample rack can be saved as a whole.

The invention is applied to an automated analyzer in which a main conveyance line for conveying sample racks is arranged between a rack supplying unit and a rack housing unit and a plurality of analysis units are arranged along the main conveyance line. According to the invention, a sample rack holding a sample is transferred from a transmission port of the rack supplying unit to the main conveyance line and is carried to an adapted analysis unit by a conveying operation of the main conveyance line. A delivery processing area is provided corresponding to each analysis unit. The sample on the sample rack is delivered to a reaction unit of the analysis unit in the delivery processing area. The delivery processing area has a reception port for receiving the sample rack from the main conveyance line and a transmission port for transmitting the sample rack to the main conveyance line. The rack housing unit has a reception port for receiving the sample rack from the main conveyance line.

Each conveyance path is determined by a combination of one of a plurality of transmission ports and one of a plurality of reception ports and a plurality of conveyance paths are determined as a whole. A controller for controlling the conveyance of the sample rack selects the conveyance path adapted to the sample rack positioned at an arbitrary transmission port from the plurality of conveyance paths and allows the sample rack to be conveyed to a reception port of the selected conveyance path. The conveyance is executed in a state where no other sample racks exist on the main conveyance line and is executed after confirming that the reception port as a receiving side is ready to receive the sample rack.

DETAILED DESCRIPTION OF THE PREFERRED EMBODIMENTS

Embodiments according to the invention will be described with reference to the drawings.

Figure 1:
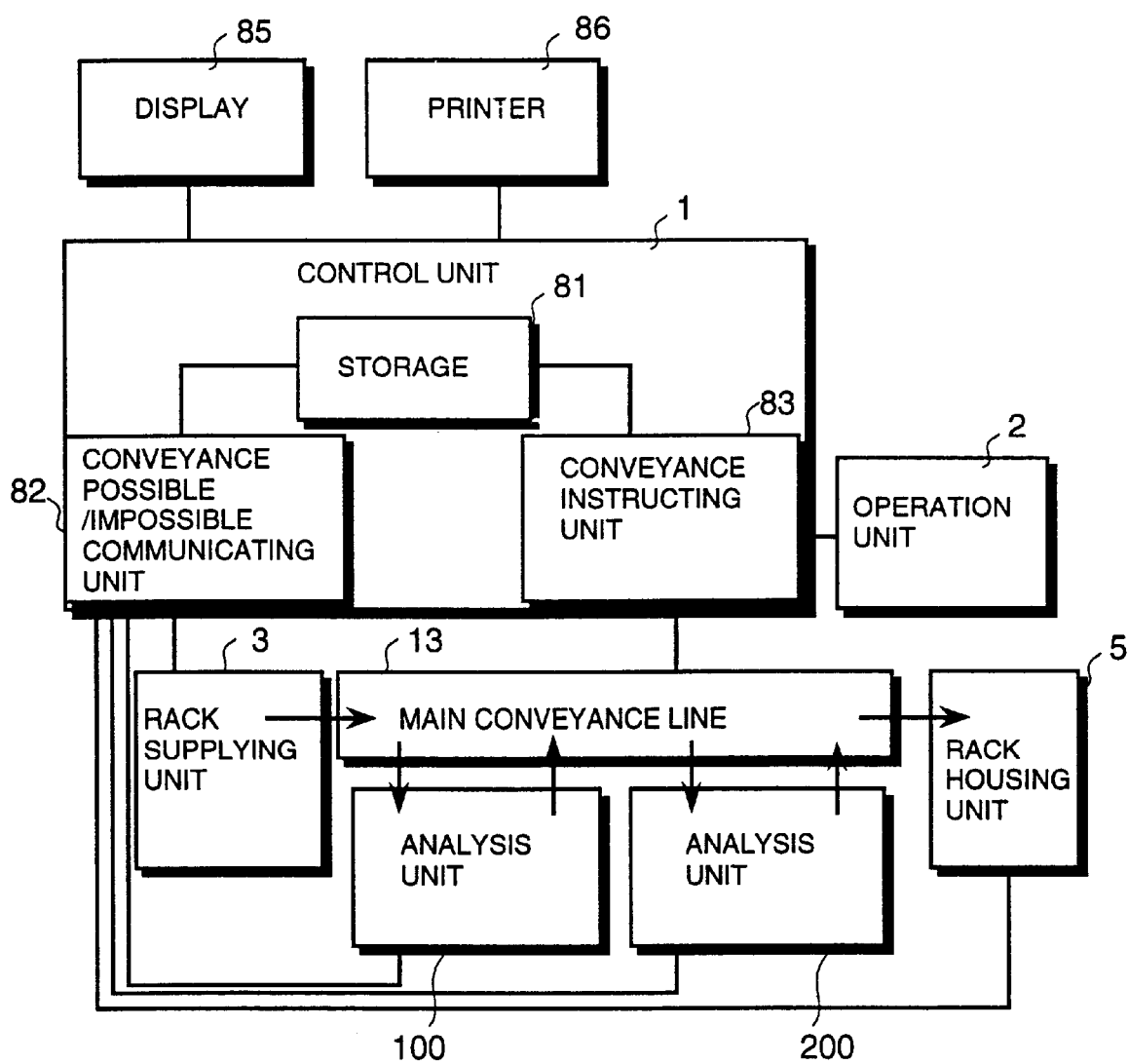
FIG. 1 is a block diagram of an automated analyzer according to an embodiment of the invention.

FIG. 1 is a block diagram of an automated analyzer according to an embodiment of the invention. In FIG. 1, a control unit 1 for controlling operations of mechanisms in the automated analyzer includes a storage 81, a conveyance possible/impossible communicating unit 82, a conveyance instructing unit 83, and the like. Samples are conveyed to an analysis unit 100 and/or an analysis unit 200 on the basis of analysis request information inputted by an operation unit 2. Analysis results are collected from the analysis units and are outputted to a picture display 85 such as a CRT and a printer 86. The control unit 1 collects information as to whether each of the units can transmit or receive the sample rack or not by the conveyance possible/impossible communicating unit 82. When both of the reception and transmission states are satisfied, a timer in the control unit 1 is started and elapsed time of each conveyance path is stored in the storage. Each time the conveying process of a main conveyance line 13 is finished, the conveyance instructing unit 83 sends an instruction to convey the next sample rack to the selected conveyance path.

Analysis items requested to examine each sample, a sample ID for identifying the sample, and sample attribute information (sex, age, kind of sample, and the like) are inputted from the operating part 2. Each sample is analyzed with respect to the analysis items by the analysis units 100 and 200 on the basis of the instruction from the control unit 1. After that, the analysis results are outputted. In a rack supplying unit 3 into which a sample rack holding a sample is loaded, the user can place a plurality of sample racks. The sample racks are supplied to the main conveyance line 13 in accordance with the placement order as a conveying process of the apparatus is advanced. A space in which an urgent sample is put so as to interrupt general samples arranged in a rack tray on which a number of racks for general sample are arranged and to be processed is provided in the rack supplying unit 3. The sample put in the space is treated as an urgent sample and is conveyed prior to the others.

The main conveyance line 13 is controlled by the control unit 1 and conveys only one sample rack at a time. The sample rack subjected to a delivery process by the analysis units 100 and 200 is housed in a rack housing unit 5 for housing a delivery-processed sample rack. Each analysis unit receives the sample rack from the main conveyance line 13, executes a delivering process, and returns the rack to the main conveyance line 13. The user can take out each rack tray having the processed racks. The analysis units 100 and 200 analyze the samples with respect to only the analysis items allocated by the control unit 1 among the analysis items inputted from the operating unit 2. Each of the analysis units 100 and 200 can have a computer as a child control unit for taking charge of a part of the functions of the control unit 1. In this case, the child control unit reports a rack transmission request and a rack reception request to the computer as a parent control unit when the rack is transmitted/received between the main conveyance line and the analysis unit. The parent control unit can control the transmission and reception of the racks by selecting one set of the requests while cooperating and communicating with the other units.

Figure 11:
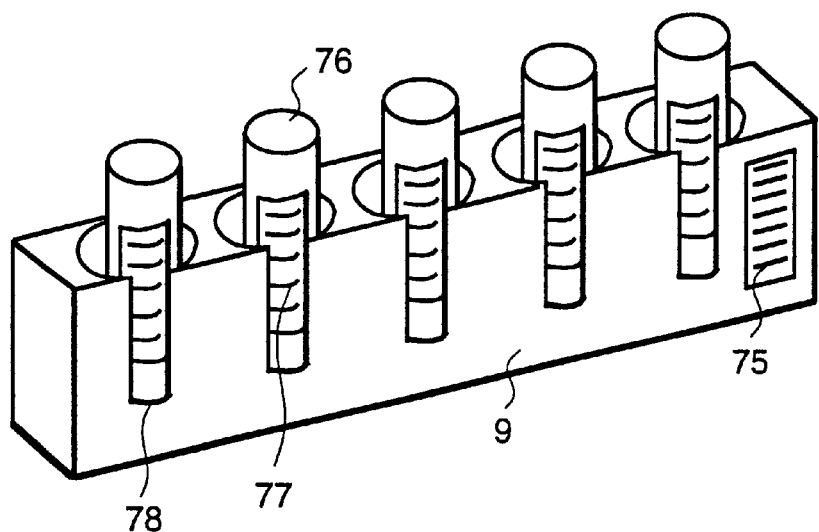
FIG. 11 is a diagram showing an example of a sample rack.

An example of a sample rack is shown in FIG. 11. A sample rack 9 can hold a plurality of sample vessels 76. The sample vessels 76 are loaded into a plurality of loading holes each having a notch 78 as a window for reading a bar code 77. A sample to be analyzed such as blood serum, blood plasma, or urine by the analysis unit is housed in each sample vessel 76. Each sample rack 9 has a plurality of holes as code information indicative of a rack number or a bar code label 75 on which a bar code is printed. The rack number identification information is read by a known reader. A magnetic record medium or the bar code label 77 is attached as a sample identification information medium on the outer wall of the sample vessel 76. The sample identification information is read out by a known reader. Since the analysis items requested for each sample are stored in the control unit 1, by recognizing the sample ID corresponding to the sample vessel, the sample rack 9 holding the sample vessel is conveyed to a corresponding analysis unit for performing analysis with respect to the relevant analysis items. One of methods of recognizing the sample ID is to directly read the ID information of the sample vessel. According to another method, a combination of an arrangement position of each sample vessel on the sample rack and a rack number is related to a sample ID and is preliminarily stored and the rack number is read. Although five test tubes are retained in the example of FIG. 11, the number of sample vessels is not limited to five but the rack can retain more than one or ten test tubes.

Figure 2:
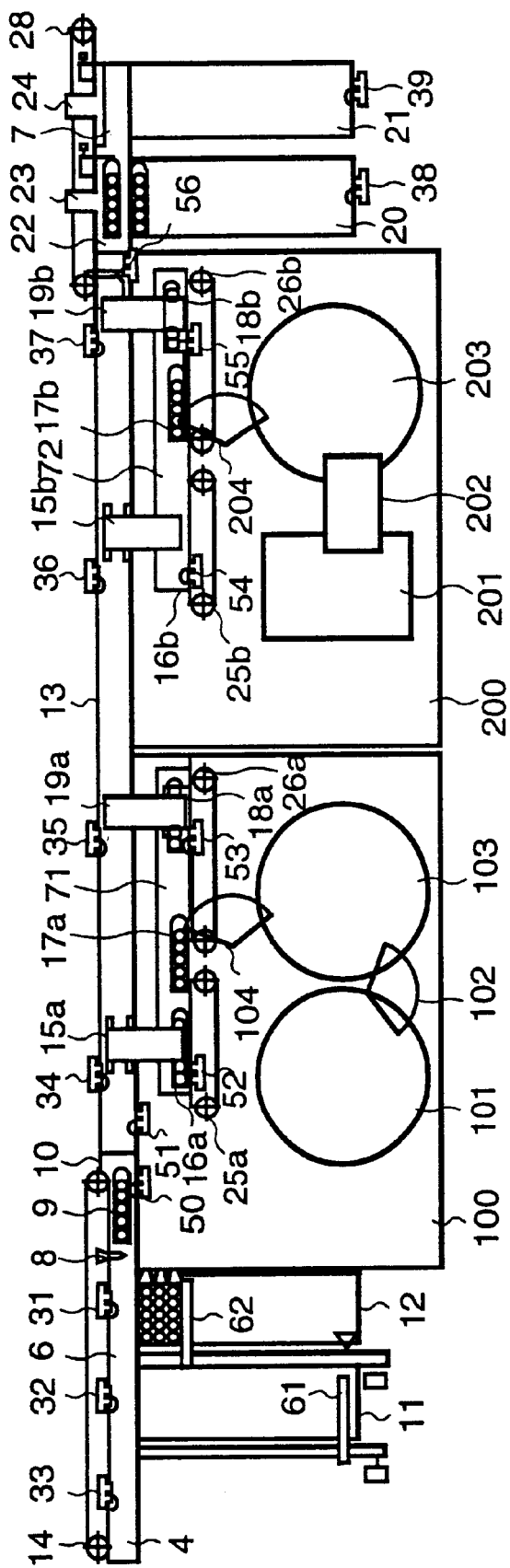
FIG. 2 is a diagram showing a construction of a part around a main conveyance line in the automated analyzer of FIG. 1.

FIG. 2 is a diagram showing a construction of a part around the main conveyance line in the automated analyzer of FIG. 1. The rack supplying unit 3 has: a plurality of rack trays 11 and 12 in which a plurality of sample racks 9 can be arranged in a specified direction; a conveyance path 6 for loading; and movable arms 61 and 62 for moving the sample racks on the rack trays to the conveyance path 6 for loading. One end of the conveyance path 6 for loading is adjacent to the main conveyance line 13 and serves as a transmission port 10 where the sample rack 9 is temporarily stopped before being carried by the main conveyance path 13. The other end of the conveyance path 6 for loading serves as an urgent sample loading port 4 from which a sample rack for an urgent test is loaded. The sample rack loaded to the urgent sample loading port 4 is detected by a rack detector 33. A detection signal is transmitted to the control unit 1. The control unit 1 is programmed to convey the urgent test sample rack prior to other general sample racks from the rack trays 11 and 12. The rack trays 11 and 12 are detachable and can be replaced by other rack trays.

A sample rack pushed from the rack tray 11 to the conveyance path 6 for loading is detected by a rack detector 32. A sample rack pushed from the rack tray 12 to the conveyance path 6 for loading is detected by a rack detector 31. A rack moving device 14 having a movable hook 8 rotates or reciprocates a belt on which the movable hook 8 is attached to move the sample rack on the loading conveyance path 6 to the main conveyance line 13. Rack identification information or sample vessel identification information of the sample rack 9 positioned at the transmission port 10 is read by an identification information reader 50 such as a bar code reader and the sample ID is recognized by the control unit 1. The kinds of analysis items which can be analyzed by analysis units are registered in the storage 81 of the control unit 1. Which one of the analysis units 100 and 200 analyzes the sample on the sample rack 9 is determined by the control unit 1 in accordance with the recognition of the sample ID and a reception port for receiving the relevant sample rack 9 is decided.

The rack housing unit 5 has: a plurality of rack trays 20 and 21 which can house a number of sample racks by arranging them in a specific direction; a conveyance path 7 for housing; and pushing devices 23 and 24 for pushing the sample rack on the conveyance path 7 to the rack trays. The main conveyance line 13 side of the housing conveyance path 7 has a reception port 22 for receiving the sample rack from the main conveyance line. Arrival of the sample rack at the reception port 22 is detected by a rack detector 56. A rack moving device 28 conveys the sample rack at the reception port 22 to a place in front of the rack tray 20 or 21 and has a construction similar to that of the rack moving device 14. Rack detectors 38 and 39 detect that the rack trays 20 and 21 are filled with racks.

The plurality of analysis units 100 and 200 are arranged along the main conveyance line 13. The analysis unit 100 has: a reagent turntable 101 which can position a reagent bottle according to the analysis item to a reagent suction position; a reaction disk 103 on which a number of reaction vessels are circularly arranged; a reagent delivery mechanism 102 for delivering a desired reagent liquid on the reagent turntable 101 to the reaction vessel on the reaction disk 103 by a pipet nozzle; and a sample delivering device 104 for delivering the sample from the sample rack on a delivery processing area 71 to the reaction vessel on the reaction disk 103 by a pipet nozzle. The analysis unit 200 has: a reagent house in which a number of reagent bottles are placed; a reaction disk 203 on which a number of reaction vessels are circularly arranged; a reagent delivery mechanism 202 having a pipe system from each reagent bottle in the reagent house 201 to the reaction disk 203 and a dispenser pump; and a sample delivery device 204 for delivering the sample from the sample rack in a delivery processing area 72 to the reaction vessel on the reaction disk 203 by a pipet nozzle. A multi-wavelength photometer, a vessel cleaning mechanism, a stirring mechanism, and the like are arranged near each of the reaction disks 103 and 203. With the above elements, a reaction part in each analysis unit is constructed. From the reaction liquid formed by mixing the sample and reagent in the reaction vessel, the wavelength according to each analysis item is selected and measured.

The delivery processing area 71 provided between the main conveyance line 13 and the reaction part of the analysis unit 100 and a delivery processing area 72 provided between the main conveyance line 13 and the reaction part of the analysis unit 200 have similar constructions. The main conveyance line 13 is constructed by a single belt rotated in a predetermined direction by a pulse motor as a driving source and can change a movement distance of the sample rack according to the number of pulses given to the driving source. A plurality of rack detectors are arranged along the main conveyance line 13. A rack detector 51 detects that the sample rack rides on the main conveyance line. Rack detectors 34 and 36 detect the sample rack for being transferred to the delivery processing areas 71 and 72. Rack detectors 35 and 37 detect that the sample rack is transferred from the delivery processing areas 71 and 72 to the main conveyance line 13.

The delivery processing areas 71 and 72 have reception ports 16a and 16b of the sample rack, delivery ports 17a and 17b, and transmission ports 18a and 18b of the sample rack which correspond each other, respectively. Rack detectors 52 and 54 detect that the reception ports 16a and 16b receive the sample racks, respectively. Rack detectors 53 and 55 detect arrival of the sample racks at the transmission ports 18a and 18b. Rack transfer devices 25a and 25b are mechanisms for transferring the sample racks at the reception ports 16a and 16b to the delivery ports 17a and 17b. Rack transfer devices 26a and 26b are mechanisms for transferring the sample racks at the delivery ports 17a and 17b to the transmission ports 18a and 18b. Each of the rack transfer devices has a construction such that a belt to which a movable hook is attached for pushing and moving the sample rack is wound around the shaft of the motor and a pulley and the belt is rotated or reciprocated.

Figure 8A:
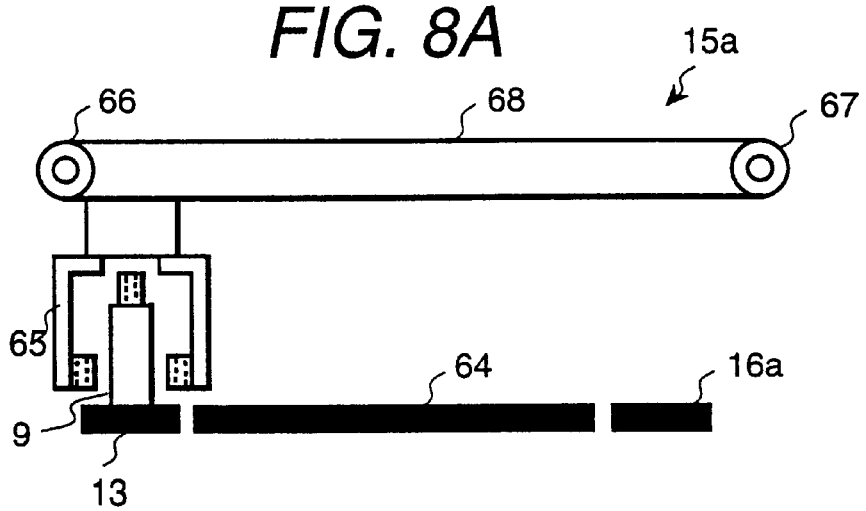
FIGS. 8(A) to 8(C) are diagrams for explaining the operation of an example of a sample transfer mechanism.
Figure 8B:
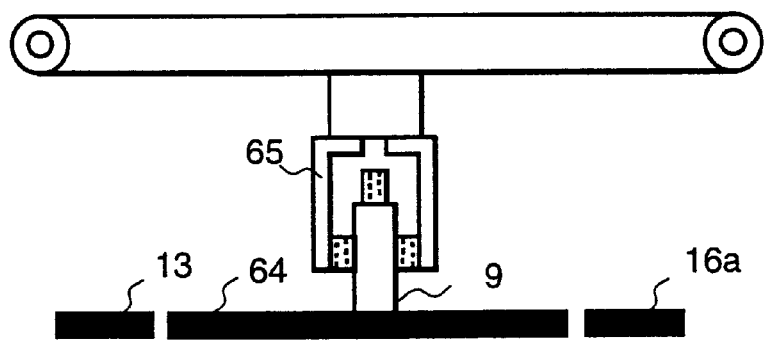
Figure 8C:
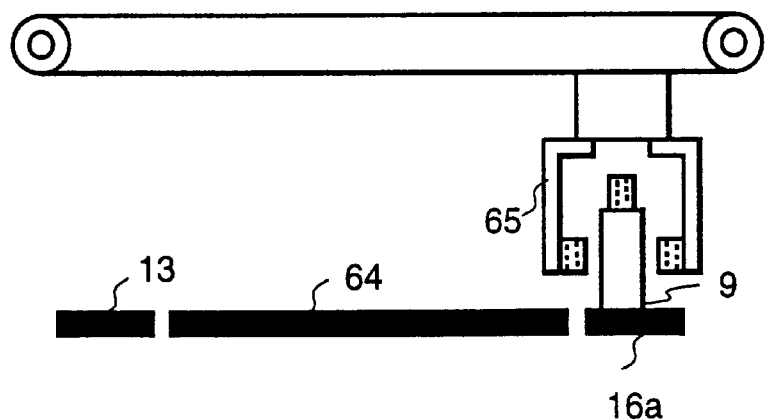

Sample transfer mechanisms 15a and 15b transfer the sample racks stopped on the main conveyance line 13 to the reception ports 16a and 16b of the delivery processing areas 71 and 72. Sample transfer mechanisms 19a and 19b transfer the sample racks at the transmission ports 18a and 18b of the delivery processing areas 71 and 72 to the main conveyance line 13. These sample transfer mechanisms have the same construction except the direction of transferring the sample racks is different. As a sample transfer mechanism, a pickup robot or a sample rack pushing mechanism can be used. An example of the sample transfer mechanism is shown in FIG. 8. In FIG. 8, a connection path 64 having a width through which the sample rack 9 can be transferred is formed between the main conveyance line 13 and the reception port 16a of the delivery area. The sample transfer mechanism 15a having a belt 68 wound around a drive shaft 66 of the motor and a pulley 67 is arranged above the connection path 64. A holding member 65 comprising a pair of fingers which can be opened and closed is attached to the belt 68. FIGS. 8A–8C. In FIGS. 8A–8C, (A) shows a state where the holding member 65 is opened and waits for the arrival of the sample rack above the main conveyance line 13. FIG. 8(B) shows a state where the holding member 65 is closed and transferring the sample rack 9. FIG. 8(C) shows a state where the sample rack 9 is carried to the reception port 16a and is released from the holding member 65.

The automated analyzer of FIG. 2 has: a reaction part for measuring a reaction liquid of a sample and a reagent corresponding to an analysis item; a mechanism for delivering the sample to a reaction vessel of the reaction part; and a mechanism for delivering a reagent selected according to the analysis item to the reaction vessel of the reaction part. The delivery processing areas 71 and 72 can be also provided in the analysis units or can be attached to the main conveyance line 13. When the sample rack is positioned in any one of the plurality of transmission ports 10, 18a, and 18b, the control unit 1 selects the reception port for receiving the sample rack from the plurality of reception ports 16a, 16b, and 22. In this case, since a plurality of conveyance paths formed by the combination of one transmission port and one reception port exist in accordance with the number of the transmission and reception ports, the control unit 1 selects the reception port adapted to the sample rack waiting to be carried at the transmission port from the plurality of conveyance paths. The sample information of each sample rack is recognized by the control unit 1 on the basis of the data read by the identification information reader 50, and the conveyance route can be easily selected.

When a single sample rack is received from one transmission port, the main conveyance line 13 is started to operate and is stopped when the sample rack reaches the target reception port or a corresponding position. During this period, the main conveyance line 13 continuously transfers the sample rack without stopping it in the middle. The control unit 1 controls the operations of the rack transfer device 14 and the sample transfer mechanisms 19a and 19b so that another sample rack is not transferred to the main conveyance line while one sample rack is conveyed. Since only single sample rack can be put on the main conveyance line, when a reception signal outputted from the rack detector of the relevant reception port is received in association with the delivery of the sample rack from the main conveyance line to the reception port, the control unit 1 discriminates that no sample rack exists on the main conveyance line. The control unit 1 determines which analysis unit analyzes the sample rack positioned at the transmission port 10 of the rack supplying part 3. If the sample rack is not adapted to any analysis unit, it is directly conveyed to the reception port 22 of the rack housing unit 5 without being stopped in the middle.

In the automated analyzer of FIG. 2, the existence of the sample rack on each transmission port is monitored by each rack detector. When the sample racks waiting to be conveyed exist on a plurality of transmission ports, the controller 1 determines which sample rack on the transmission port is preferentially delivered to the main conveyance line on the basis of a predetermined priority path. The priority path is determined based on the length of waiting time. The waiting time of the sample rack to be carried on the transmission port can be counted from a point of time when the detection signal is obtained from the rack detector of the transmission port. The counting of waiting time can be also started from a point of time when the adapted conveyance path of the sample rack positioned at each transmission port is selected, that is, from a time point when the relevant reception port is determined. The counting of the waiting time can be also started from a point of time when the relevant reception port becomes ready to receive the rack. In any case, the control unit compares the waiting time of the sample racks at the plurality of transmission ports, preferentially conveying the sample rack of the conveyance path having the longer waiting time by the main conveyance line to the target reception port. Another form of determining the priority rule is based on whether an urgent test is needed or not. The sample rack loaded to the urgent sample loading port 4 is preferentially carried by the main conveyance line by interrupting the conveying process of the general sample rack on the rack trays 11 and 12.

The automated analyzer of FIG. 2 treats a sample for calibration specially. While the sample rack holding a sample for calibration is positioned in the delivery processing area 71 or 72, the conveyance is limited so that another sample rack transmitted behind the sample rack for calibration from the transmission port 10 of the rack supplying unit 3 is not housed in the rack housing unit 5 before the sample rack for calibration. The conveyance of the sample rack holding the sample for calibration is limited so that the sample rack for calibration is housed in the rack housing part 5 after another sample rack transmitted from the transmission port 10 of the rack supplying unit 3 prior to the sample rack for calibration is housed. Such a process on the program is called a no-passing rule.

The operation of the automated analyzer of FIG. 2 will be described in detail hereinbelow.

In the rack supplying unit 3 in FIG. 2, the sample rack 9 placed on the rack tray 11 or 12 is conveyed by the movable arm to the conveyance path 6 for loading and is detected by the rack detector 31 or 32. The sample rack 9 is moved by the rack transfer device 14 and is carried by the movable hook 8 to a position just before the main conveyance line 13. When the rack loading operation is executed in one rack tray (11) but the rack is not detected by the detector, it is determined that all of the racks in the rack tray 11 were loaded, so that it is switched to load the racks from the other rack tray 12. When the sample rack is placed at the urgent sample loading port 4, it is detected by the rack detector 33 and is conveyed on the main conveyance line prior to general samples on the rack trays 11 and 12. When the identification information reader 50 which also serves as a detector detects that the sample rack has arrived at the transmission port 10 just before the main conveyance line, a conveyance request of the rack from the rack supplying unit 3 to the main conveyance line 13 is sent and the rack waits for a permission of transmission. The sample ID read by the identification information reader 50 is stored in the storage 81 of the control unit 1.

On the other hand, since the analysis units 100 and 200 and the rack housing unit 5 have no sample rack therein just after the start of the operation of the analyzer, all of them send a request of receiving racks. The rack detectors 38 and 39 provided in the rear part of the rack trays 20 and 21 detect that the rack trays 20 and 21 in the rack housing unit 5 are filled with racks. When both of the trays are full of racks, an alarm indicating that no more, racks can be carried in is displayed on the display 85.

The control unit 1 for controlling the main conveyance line periodically checks the requests from the transmission and reception ports in a determined cycle. When there is a transmission request, the receiving side of the sample rack at the transmission port which sent the transmission request is checked up on the basis of a preliminarily inputted analysis request. When the relevant reception port is ready to receive, the rack is carried in.

When the sample rack waiting at the transmission port of the rack supplying unit 3, that is, in front of the carrying port of the main conveyance line 13 requests the analysis unit 100 to analyze, a conveyance request from the transmission port 10 to the reception port 16a of the analysis unit 100 is generated. When the sample rack does not request the analysis unit 100 but requests the analysis unit 200 to analyze, the conveyance request from the main conveyance line 13 to the reception port 16b of the analysis unit 200 is generated.

FIG. 2 shows a view in which the latter request is generated, there is no sample rack on the main conveyance line, and the reception port 16b in the delivery processing area 72 of the analysis unit 200 is ready to receive, so that the sample rack at the transmission port 10 is going to be loaded on the main conveyance line 13. The sample rack is transferred to the analysis unit 200 by the seamless belt of the main conveyance line and is carried in the reception port 16b by the sample transfer mechanism 15b.

The sample rack taken by the analysis unit 200 is transferred to the delivery port 17b by the hook of the rack transfer device 25b and the sample is delivered by the sample delivery device 204. Since the sample rack for holding five test tubes is used in the example, the contents of the sample are delivered from the test tubes to the reaction vessels arranged on the circumference of the reaction disk 203 one by one by the operation of the delivery nozzle. While the reagent of the reagent house 201 is delivered by the reagent delivery mechanism 202, the reaction is progressed and the analysis of the desired item is executed. The sample rack whose contents were delivered to the reaction vessels is carried to the transmission port 18b and gives the delivery port 17b to the sample rack to be carried next. At this point of time, the analysis unit 200 sends a conveyance is request to the main conveyance line 13 and waits for the transmission permission. When the transmission is permitted, the sample rack is transferred from the transmission port 18b to the main conveyance line 13 by the sample transfer mechanism 19b and moves to the exit of the main conveyance line, that is, the reception port 22 of the rack housing unit 5. When the sample rack arrives at the analysis unit 200 and is subjected to the delivery process, since the main conveyance line 13 has no racks, the main conveyance line 13 can be used to carry the next sample rack. Further, since five test tubes are retained by one sample rack in the example, the rack is carried in and out every delivery processing time of five tubes. The operation of the main conveyance line is executed every delivery processing time of five tubes not depending on the delivery cycle of the individual analysis unit. Therefore, the conveying operation having enough time which does not depend on the fine delivery cycles can be realized.

Similarly, if the sample rack waiting at the transmission port 10 of the loading conveyance path 6 in the rack supply unit 3 to be loaded to the main conveyance line 13 is requested to be carried to the analysis unit 100, the sample rack is carried into the reception port 16a of the analysis unit 100 by a similar sequence. The sample rack taken into the analysis unit 100 is subjected to the delivery process in a manner similar to the case of the analysis unit 200. Since the analysis unit 100 has the delivery device 104, reaction disk 103, and reagent delivery mechanism 102 which are different from those in the analysis unit 200, a delivery cycle (time from one delivery to the next delivery) is different from that of the analysis unit 200. In a manner similar to the analysis unit 200, since the delivery processing area 71 is independent from the main conveyance line 13, a delivery independent from a conveying operation of the main conveyance line and a delivery of another analysis unit can be executed. The delivery processed sample rack is sent to the transmission port 18a, a request of conveyance from the transmission port 18a to the main conveyance line 13 is sent and the rack waits for a transmission permission.

When the transmission from the transmission port 18a is permitted, if all of the delivery processes with respect to the requested items are executed in the analysis unit 100, the sample rack is carried to the rack housing part 5 via the main conveyance line. However, if the sample delivered to the analysis unit 100 is requested to be analyzed also by the next analysis unit 200, a request for conveyance from the transmission port 18a at the exit of the analysis unit 100 to the reception port 16b at the entrance of the analysis unit 200 is generated. The request is received when there is no sample on the main conveyance line 13 and the reception port 16b is ready to receive the sample rack, and the conveying operation is executed.

If the sample rack waiting at the transmission port 10 of the loading conveyance path in the rack supplying unit 3 to be loaded to the main conveyance line 13 is a rack holding a sample which is not requested to be analyzed by both of the analysis units 100 and 200, a request for conveyance from the transmission port 10 to the reception port 22 as an exit of the main conveyance line is generated. When the request is accepted, the sample rack is carried to the reception port 22 by the main conveyance line and is housed into the rack tray 20 or 21 by the pushing device 23 or 24. In case of both of the requests, the conveying operation is executed only when the reception port as a receiving side is ready to receive the sample rack and there is no sample rack on the main conveyance line 13.

Figure 3:
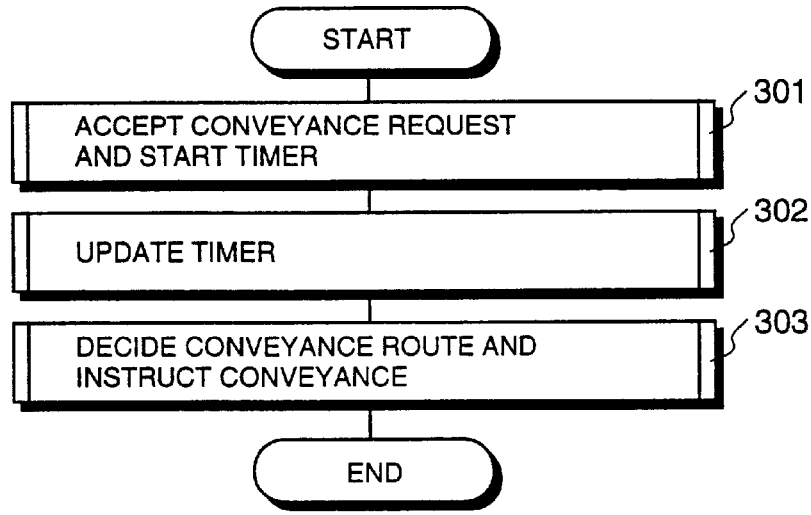
FIG. 3 is a flowchart for explaining a preparation process for determining a conveyance path of a sample rack.

FIG. 3 is a flowchart for processes from the reception of the request for conveyance until instruction of the conveying operation of the sample rack. In case of the automated analyzer of the embodiment of FIG. 2, there are the following six kinds of conveyance requests: (1) from the transmission port 10 to the reception port 16a of the analysis unit 100, (2) from the transmission port 10 to the reception port 16b of the analysis unit 200, (3) from the transmission port 10 to the reception port 22 of the rack housing unit 5, (4) from the transmission port 18a of the analysis unit 100 to the reception port 16b of the analysis unit 200, (5) from the transmission port 18a of the analysis unit 100 to the reception port 22, and (6) from the transmission port 18b of the analysis unit 200 to the reception port 22. These requests are accepted one by one and the conveying operation is executed. When there are a plurality of requests at the same time, one request to be executed first is determined on the basis of the priority order. The process of FIG. 3 is broadly divided into three processes. In a receiving process 301, when the reception side of the sample rack which is requested to be carried is ready to receive, the type of the sample (general, urgent, or the like) is stored according to the path from a transmission side (i) to a receiving side (j) and necessity and the conveyance request is accepted. The counting of time is started by a timer allocated every conveyance path. In a check process 302, the elapsed time of the timer which started the counting is updated to the newest and the time elapsed from the reception of the request is counted. In a priority conveyance determining process 303, if the rack is not being conveyed, a path for the rack having the largest elapsed time is searched and the conveyance path is determined, and the conveying operation is instructed to the main conveyance line 13. By starting the process corresponding to the flowchart periodically in the control unit 1 or each time when a state of the analysis unit is changed, all of the conveyance requests are received and the sample rack is carried.

Figure 4:
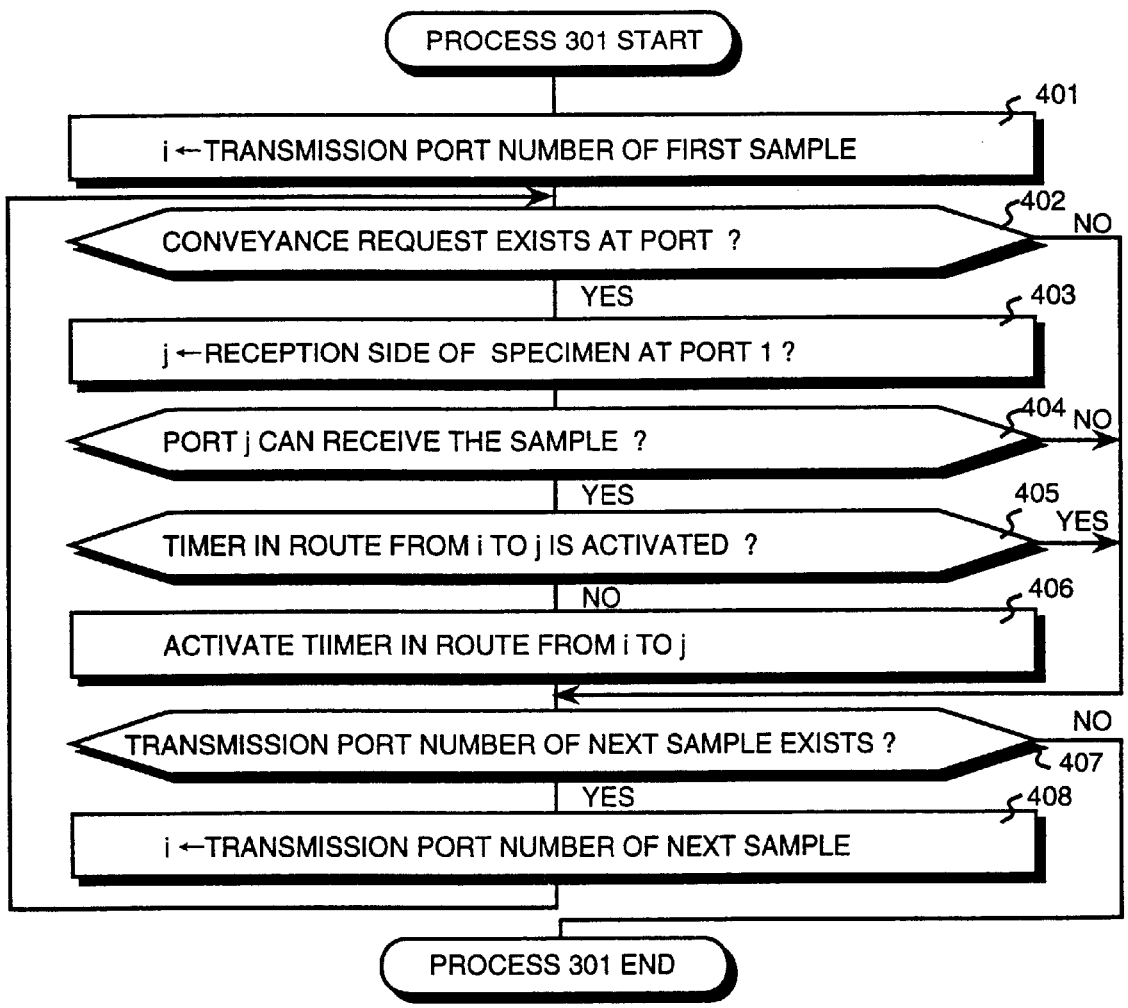
FIG. 4 is a flowchart for a detailed operation of a receiving process in FIG. 3.

FIG. 4 is a flowchart of a detailed operation of the process 301 in FIG. 3 for checking the conveyance requests of all of the transmission ports. First, the transmission port number of the first sample rack is substituted for (i) (401). In association with this, the conveyance requests from the respective transmission ports are stored. When there is no waiting rack on the transmission port, the conveyance request is not stored. When the port (i) sends the conveyance request (402), the sample ID of the sample on the rack waiting at the port is checked and the receiving side of the sample of the sample ID, that is, which analysis unit analyzes the sample with respect to the analysis requested item or whether the sample is housed, is checked. The receiving side is substituted for (j) (403) and a check is made to see whether the reception port (j) corresponding to the receiving side (j) is ready to receive the sample rack or not (404). If YES, whether the timer of the conveyance path from (i) to (j) is started or not is checked (405). All of the timers are stopped at the start of the analysis. When the timer is not started, a timer on the conveyance path from (i) to (j) is started and the conveyance request is stored (406). In other words, the conveyance path on which the timer is started denotes a path which received the conveyance request. The process of the conveyance request at the port (i) has been completed. After that, whether a next transmission port number exists or not is checked (407). If there is a rack at the next transmission port, the transmission port number is substituted for (i) (408) and the processes from step 402 are repeated. After the processes are repeated until the conveyance request of the last transmission port is checked, the process 301 is finished. The processing routine advances to a process of 302. The transmission port numbers in the diagram are consecutive numbers allocated to the transmission ports 10, 18a, and 18b. On the contrary, the reception port numbers (j in the diagram) are consecutive numbers allocated to the reception ports 16a, 16b, and 22.

Figure 5:
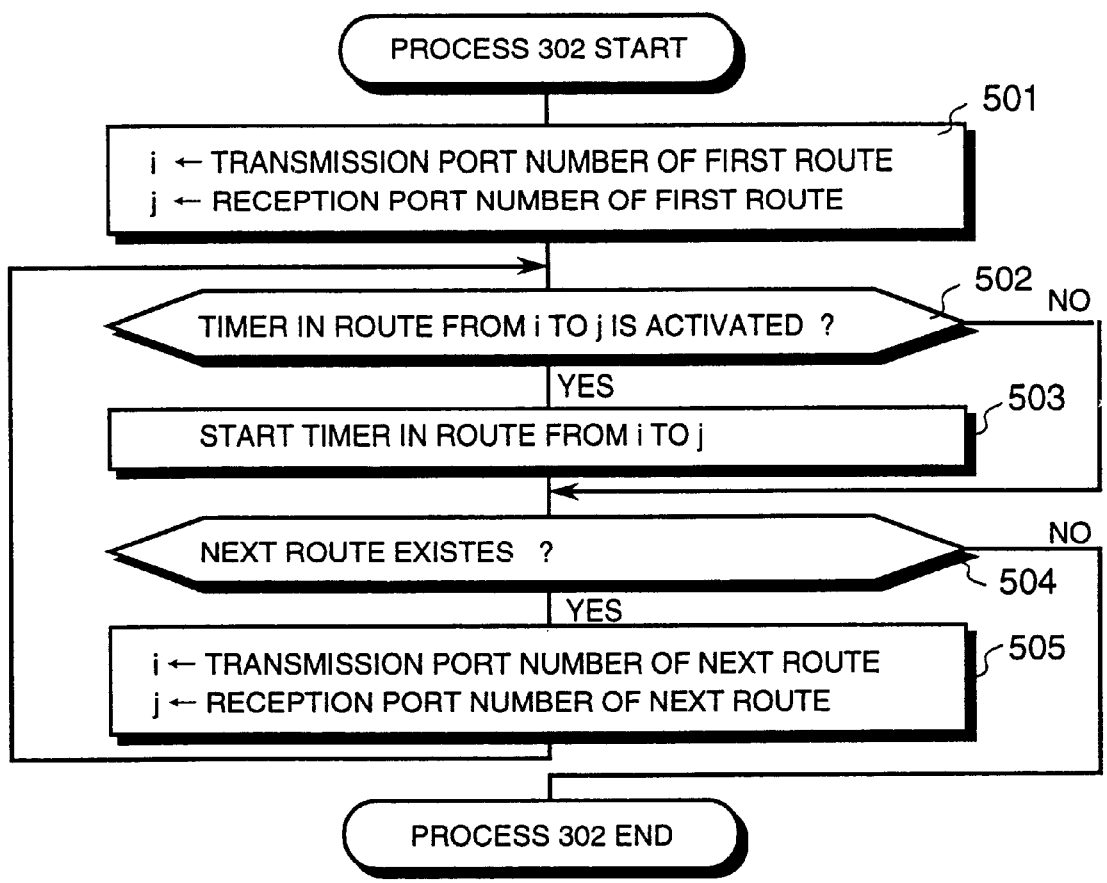
FIG. 5 is a flowchart for a detailed operation of a checking process in FIG. 3.

FIG. 5 is a flowchart of a detailed operation of the process 302 in FIG. 3. First, the transmission port number of the first conveyance path is substituted for (i) and the reception port of the conveyance path is substituted for (j) (501). A check is made to see whether a timer on the path from the transmission port (i) to the reception port (j) is activated or not (502). If the timer is activated, the counting of time of the conveyance path from (i) to (j) is started (503). After that, whether the next path exists or not is checked (504). If YES, the transmission port number is substituted for (i) and the reception port number is substituted for (j) (505), and the processes from step 502 are repeated. If there is no path, the process 302 is finished and the processing routine advances to the next process 303.

Figure 6:
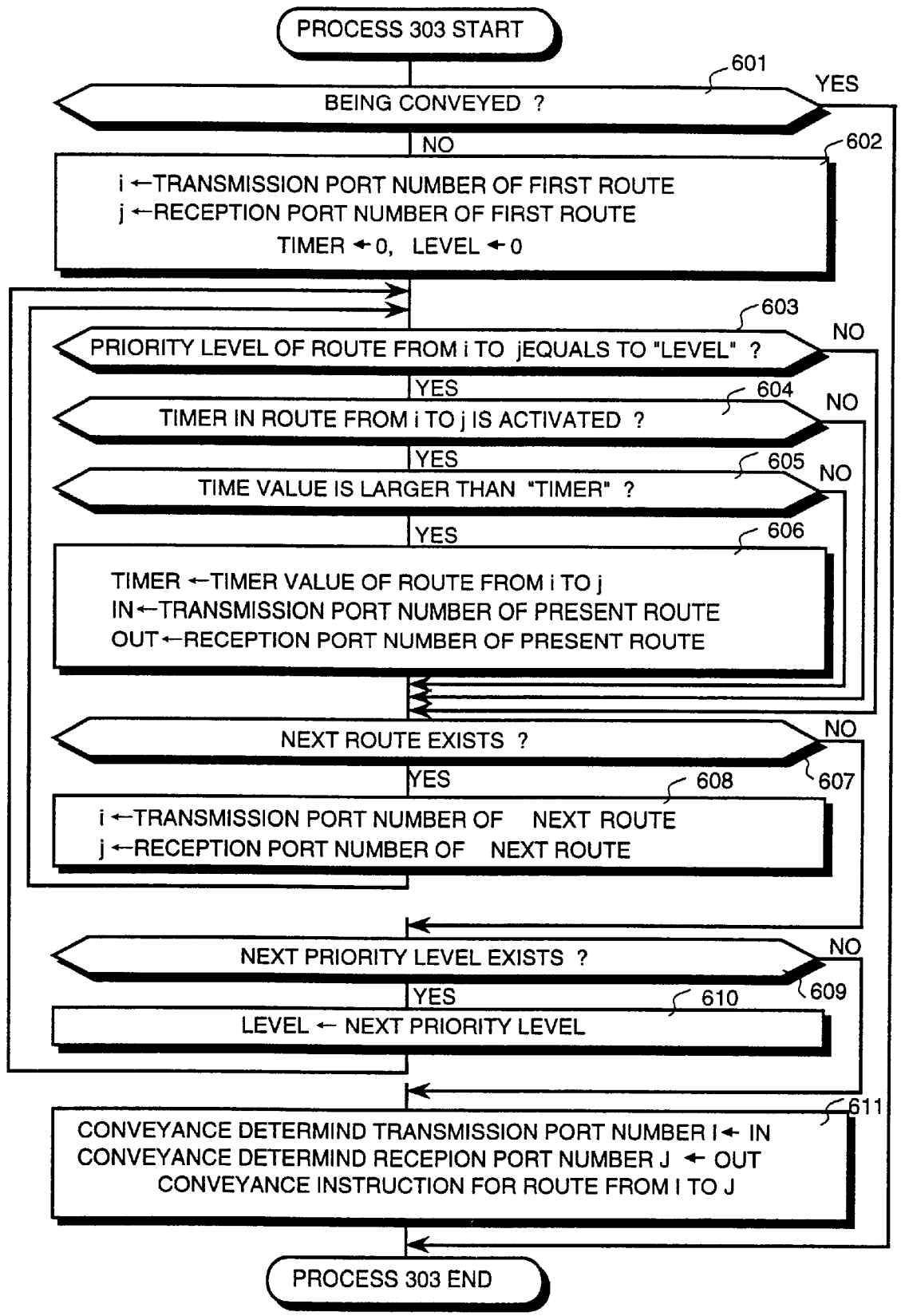
FIG. 6 is a flowchart for a detailed operation of a preferential conveyance determining process in FIG. 3.

FIG. 6 is a flowchart of a detailed operation of the process 303 in FIG. 3. First, whether the main conveyance line 13 is conveying the sample rack or not is checked. If YES, the process 303 is finished (601). If NO, the conveyance path is determined. In order to determine the first path, variables are initialized in such a manner that the number of the first transmission port having the sample rack is substituted for (i), the corresponding reception port number is substituted for (j), 0 is substituted for "timer" as a variable of elapsed time, 0 is substituted for "level" indicative of thee degree of urgency (602). In the embodiment, the highest priority level is set to 0 (urgent sample) and the rack on the path waiting longest is preferentially selected from the racks at the highest level. A check is made to see whether the priority level of the conveyance path from (i) to (j) is equal to "level" or not (603). If NO, a next path is searched (607). If YES, whether the timer on the path from (i) to (j) is activated or not is checked (604). If the timer is not activated, the next path is searched (607). If it is activated, the timer value of the path is compared with the value of "timer" (605). If the timer value is equal to or smaller than "timer", the next path is searched (607). If the timer value is larger than "timer", the timer value is substituted for "timer", the transmission port number (i) is substituted for "in", and the reception port number (j) is substituted for "out", respectively (606). After that, a check is made to see whether the next path exists or not. If YES in step 607, the transmission port number of the path is substituted for (i) and the reception port number is substituted for (j) (608). The processes from step 603 to step 608 are repeated. If there is no next path, a check is made to see whether there is the next priority order level (609). The level is substituted for "level" (610) and the processes from step 603 are repeated. When the process is executed until the lowest level and there is no more priority order, all of the conveyance paths at all of the levels were checked. Therefore, an instruction of conveyance is sent to the main conveyance line by substituting the decided transmission port number of the conveyance path whose "in" and "out" values are determined for (I), and by substituting the received reception port number for (J) (611).

As mentioned above, the racks are processed from the rack having longer waiting time, so that the conveyance with little variation can be realized. The timer can be also started from a point of time of the arrival of the sample rack at the transmission port. By storing the accumulated waiting time of each sample rack, the sample rack having longest time since it entered the system can be also preferentially carried. The rack may be also preferentially carried in accordance with the loading order of the racks either by numbering the racks in accordance with the loading order to the system or by writing time when the rack is loaded to the system.

Figure 7:
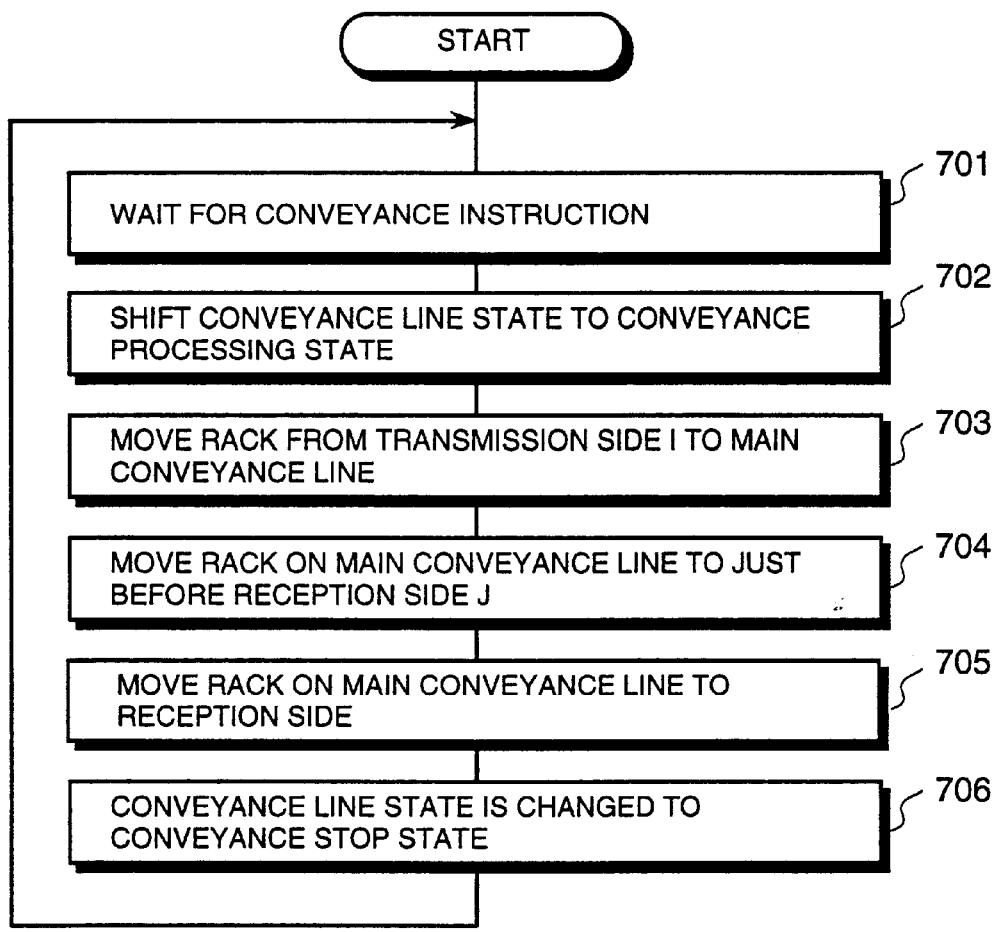
FIG. 7 is a flowchart for a conveying process indicative of movement of the sample rack in association with the conveyance.

FIG. 7 is a flowchart of a conveying process showing the movement of the sample rack in association with the conveyance. A case where the sample rack 9 is conveyed from the delivery processing area 71 of the analysis unit 100 in FIG. 2 to the delivery processing area 72 in the analysis unit 200 will be described. The process for conveying the sample rack is started by receiving the conveyance request from each port (701). When numbers I and J of the conveyance path from the transmission port 18a to the reception port 16b determined by the preparing process of FIG. 3 are received, the control unit shifts the control state of the main conveyance line to a conveyance processing state (702). A transmission instruction of a rack from the transmission port 18a as a sample rack transmitting source is sent and the sample rack 9 is moved from the transmission port 18a to the main conveyance line 13 by the sample transfer mechanism 19a (703). When it is detected by the rack detector 53 that there is no sample rack on the transmission port 18a and it is confirmed by the rack detector 35 that the sample rack is transferred to the main conveyance line 13, the control unit 1 recognizes the completion of the transfer. After the transfer of the sample rack to the main conveyance line 13 is confirmed, the main conveyance line is driven by a distance to a position corresponding to the reception port 16b as a reception side J and is stopped (704).

When the sample rack on the main conveyance line 13 is detected by the rack detector 36, the sample transfer mechanism 15b is instructed to move the sample rack from the main conveyance line to the reception port 16b (705). Simultaneously, an instruction to return the sample transfer mechanism 19a on the delivery processing area 71 side to the original state is sent. It is detected by the rack detector 54 that the sample rack is transferred to the reception port 16b by the sample transfer mechanism 15b on the analysis unit 200 side and it is recognized that the sample rack is taken in the delivery processing area 72. The control unit 1, accordingly, finishes the rack conveyance operation in the conveyance path from I to J, that is, the conveyance path from the transmission port 18a to the reception port 16b. The control unit 1 shifts the control state of the main conveyance line to a conveyance stop state and enters a waiting state for a next conveyance instruction (706). The main conveyance line is driven while communicating the other mechanisms relating the conveyance from the reception of the conveyance request of the sample rack to the end of the conveyance to the reception side with respect to one conveyance path, thereby conveying only one sample rack at a time and preventing a useless waiting time.

According to the example of FIG. 7, the pulse motor as a driving source of the belt conveyor of the main conveyance line 13 is driven so as to move the sample rack by a distance from a position corresponding to the transmission port of the sample rack to a position corresponding to the reception port. It can be also constructed that, in order to improve accuracy of the stopping position of the sample rack on the main conveyance line 13, a blocking arm for blocking the movement of the sample rack at a position corresponding to the port on the main conveyance line 13 descends according to the selected conveyance path to block the transfer path of the sample rack. The blocking arm provided corresponding to each stop position is usually opened. The sample transfer mechanisms 15a and 15b for loading the sample rack from the main conveyance line to the delivery processing area in FIG. 2 and the sample transfer mechanisms 19a and 19b for transferring the sample rack from the delivery processing area to the main conveyance line can be independently operated, respectively. Consequently, the receiving and transmitting operations of the sample racks can be also carried out in parallel.

Figure 9:
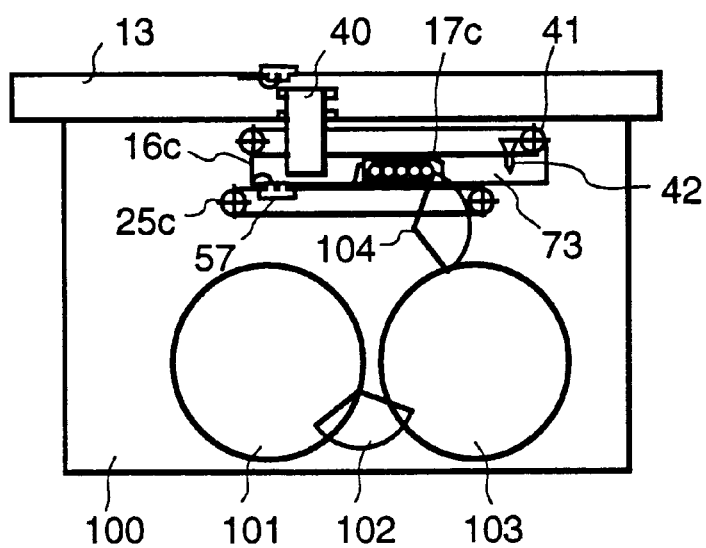
FIG. 9 is a diagram showing a main part of another embodiment according to the invention.

FIG. 9 is a diagram showing a main part of another embodiment based on the invention. In the example of FIG.

9, although a method of transferring the sample rack between the delivery processing area and the main conveyance line is different from that of the example of FIG. 2, the other construction is substantially the same as that of FIG. 2. In FIG. 9, the delivery processing area 73 in the analysis unit 100 has a dual port 16c serving as both of reception and transmission ports. The sample rack is moved bidirectionally by one sample transfer mechanism 40 between the main conveyance line 13 and the delivery processing area 73. The sample rack moved from the main conveyance line 13 to the dual port 16c by the sample transfer mechanism 40 is detected by the rack detector 57. The sample rack is moved by the movable hook of the rack transfer device 25c to the delivery port 17c. The sample on the rack is delivered to the reaction vessel on the reaction disk 103 by the sample delivery device 104. The sample rack subjected to the delivery process is returned to the dual port 16c by the movable hook 42 of the rack transfer device 41. By a following permission of conveyance, the sample rack is transferred to the main conveyance line 13 by the sample transfer mechanism 40. In case of the delivery processing area 73 as shown in FIG. 9, the next sample rack can be accepted only when there is no sample rack in the area.

An analysis unit for only receiving the sample rack from the main conveyance line may be also provided as one of the plurality of analysis units arranged along the main conveyance line 13 as shown in FIG. 2. In this case, the sample rack transferred to the analysis unit side is not returned to the main conveyance line. Contrarily, an analysis unit for only transmitting the sample rack to the main conveyance line can be also arranged along the main conveyance line. In the automated analyzer of FIG. 2, three or more various analysis units can be mixedly connected. In such a case as well, the conveyance of the sample rack can be controlled without changing the above-mentioned procedure.

The automated analyzer of FIG. 2 has a function such that while a specific rack having a special sample exists in the delivery processing area 71 or 72, the conveyance of the sample rack is controlled so as not to be passed by the rack for the general sample. There are a plurality of examples of such a no-passing rule. One of them relates to a case where a control sample is measured every predetermined number of samples for controlling inspection quality. In this case, the conveyance is controlled in such a manner that a rack of the control sample cannot pass a sample rack which entered before the control sample rack in order to keep a constant value and a sample rack which entered after the control sample rack cannot pass the control sample rack. According to the invention, in order to deal with the special sample, the no-passing rule of racks is established. If there is a rack which cannot be passed according to the no-passing rule on the analysis unit side when a rack to be transmitted is selected at the transmission port to the main conveyance line, it is not transmitted. Consequently, waiting time during which other racks are subjected to the delivery process can be shortened and the analyzer can also cope with an operation in which the rack is not passed.

With respect to a sample necessary to be reexamined, a reexamination buffer is provided at the exit of the main conveyance line, the sample returns from the exit of the reexamination buffer and passes the line again, thereby returning the sample to the transmission port of the rack supplying unit. Thus, it is not necessary to change the above-mentioned procedure.

According to the foregoing embodiment, the delivery of the sample in the delivery processing area and the conveyance of the sample rack by the main conveyance line can be executed without obtaining synchronization. Since the sample rack whose reception side is determined bypasses the analysis unit which is not designated and is conveyed to the next analysis unit, a surplus waiting time can be eliminated upon transfer of the sample rack.

Figure 10:
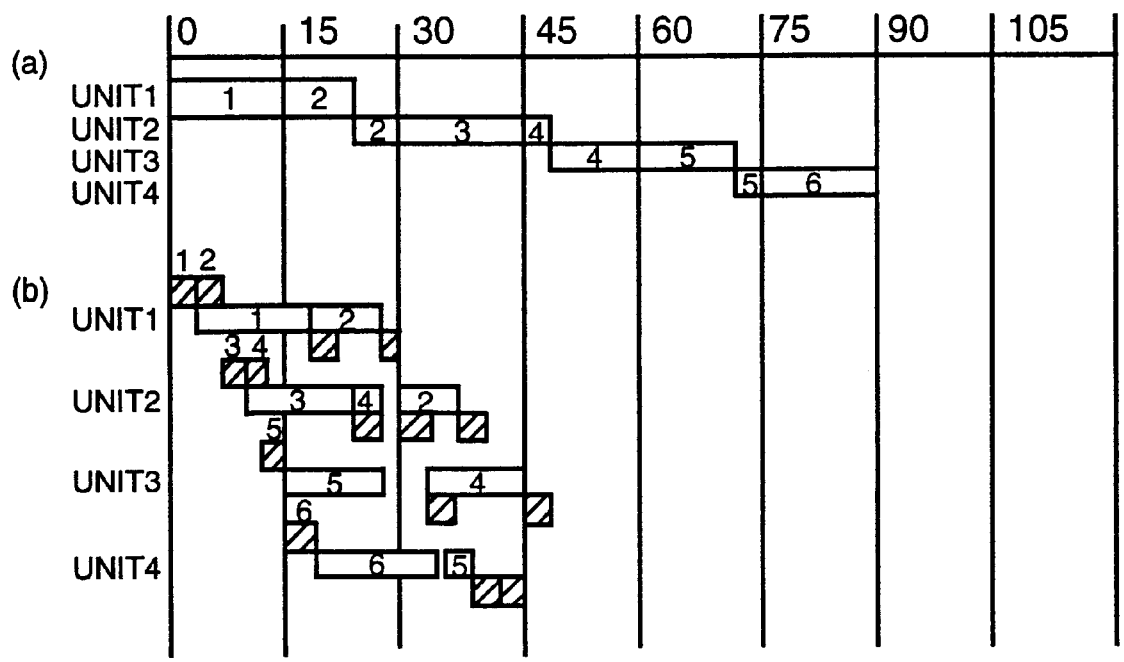
FIG. 10 is a diagram in which sample rack processing time in a case where the invention is applied is compared with that of a case where the invention is not applied.

FIG. 10 is a diagram in which the delivery processing time of the sample rack in a case (a) to which the invention is not applied is compared with that of a case (b) to which the invention is applied. Both of FIGS. 10(a) and (b) show results of simulation in which a group of sample racks are conveyed in an automated analyzer in which four analysis units are arranged along the main conveyance line. The example for comparison of FIG. 10(a) relates to a method in which the sample rack is periodically sent from the rack supplying unit to the main conveyance line, a plurality of sample racks are arranged on the main conveyance line, and the sample delivery process is performed while keeping the sample racks on the main conveyance line. Therefore, the rack entered later on the main conveyance line is subjected to the delivery process after the delivery process to the previous rack is finished. In FIG. 10(a), 90 seconds was required to process six racks of Nos. 1 to 6.

On the contrary, according to the example of FIG. 10(b) to which the invention is applied, time required for processing six racks is 48 seconds and time of 42 seconds is shortened as compared with FIG. 10(a). The axis of abscissa of FIG. 10 shows time (seconds) elapsed from the start of the analysis. The axis of ordinate shows that four analysis units (No. 1 to No. 4 units) are sequentially connected via the main conveyance line from the upstream side of the main conveyance line. In FIG. 10, blank rectangles show stop time of the rack for the sample delivery at each analysis unit and numbers in the rectangles show rack numbers. Hatched rectangles show time when the rack is conveyed by the main conveyance line and numbers out of the rectangles show rack numbers when the conveyance is started in the system. In the example, the delivery process is executed to the No. 1 rack for 15 seconds and to the No. 2 rack for 9 seconds in the analysis unit No. 1. The delivery process is executed to the No. 2 rack for 6 seconds, to the No. 3 rack for 15 seconds, and to the No. 4 rack for 3 seconds in the analysis unit No. 2. The delivery process is performed to No. 4 rack for 12 seconds and to No. 5 rack for 12 seconds in the analysis unit No. 3. Further, the delivery process is executed to the No. 5 rack for 3 seconds and to the No. 6 rack for 15 seconds in the analysis unit No. 4.

In case of the comparison example of FIG. 10(a), the next rack cannot be delivery processed unless the delivery process to the previous rack is finished. In case of the example of FIG. 10(b) to which the invention is applied, the relevant sample rack can be directly conveyed to the analysis unit as the receiving side by skipping the analysis unit which is not designated. Consequently, the waiting time upon transfer of the rack can be shortened and the whole time since the conveyance is started until the rack is housed can be accordingly shortened. The No. 3 and No. 4 racks are conveyed to the analysis unit No. 2 and are delivery processed while the delivery process to the No. 1 rack and the No. 2 rack is executed by the analysis unit No. 1. Similarly, the No. 5 and No. 6 racks are directly conveyed to the first designated analysis units, respectively. As mentioned above, by conveying the single sample rack at a time, efficiency of the parallel processes of the plurality of sample racks can be improved. Although the case where the number of sample racks to be housed in the delivery processing area of each analysis unit is one was described in the simulation example of FIG. 10, by using two or more housing racks, the time can be further shortened.

According to the embodiment as mentioned above, both of the analysis units for processing a large amount of the samples with respect to a few kinds of analysis items and the analysis unit for processing a small amount of the samples with respect to various kinds of analysis items can be included in one automated analyzer. Since it is unnecessary to take the sample rack to the analysis unit which is not designated, the conveyance time and the delivery work time can be remarkably saved. When there is an urgent sample, it can be easily conveyed prior to the general samples. Therefore, the automated analyzer which is preferably used by the urgent sample can be provided. In the case where the plurality of sample racks wait to be conveyed, the waiting time is monitored for every sample rack, and the sample rack having a longer waiting time is preferentially conveyed. Consequently, the process which is efficient to each sample rack can be realized.

According to the invention, after the information that the receiving side analysis unit adapted to the test target of the sample on the sample rack at the transmission side is ready to receive is obtained, the sample rack is conveyed by the main conveyance line. Consequently, the sample rack is not conveyed by passing useless paths and time required for the conveyance can be reduced as a whole. Since the main conveyance line conveys the sample rack one by one, the sample rack being conveyed is not disturbed by other sample racks on the main conveyance line but is promptly conveyed to a desired reception side. Further, by setting the priority order of the conveyance, a certain sample rack is not left without being conveyed for abnormally long time.

What is claimed is:

1. A method of conveying a sample rack supplied from a rack supply device through a main conveyance line to at least one of a plurality of analysis units, causing the sample rack to be subjected to a pipetting process for a sample held thereby, in the analysis unit to which the sample rack is conveyed, and conveying the sample rack subjected to the pipetting process to a rack housing device through the main conveyance device, the method comprising:

(1) controlling transferring operations of ordinary sample racks so that when a first ordinary sample rack which starts to be transferred by the main conveyance line needs to be received by a specific analysis unit and a second ordinary sample rack which starts to be transferred by the main conveyance line after the first ordinary sample rack starts to be transferred thereby does not need to be received by the specific analysis unit, the second ordinary sample rack bypasses the specific analysis unit to be transferred towards the rack housing device while the first sample rack is received by the specific analysis unit, and (2) controlling transferring operations of control sample racks and ordinary sample racks so that when an ordinary sample rack starts to be transferred by the main conveyance line after a control sample rack holding a control sample starts to be transferred thereby, the following ordinary sample rack is housed by the rack housing device after the preceding control sample rack is housed thereby.

2. The method according to claim 1, which further comprises controlling transferring operations of the control sample racks and ordinary sample racks so that when there is another ordinary sample rack to be transferred by the main conveyance line in advance of the control sample rack, the control sample rack is housed by the rack housing device after another ordinary sample rack mentioned above is housed thereby.

3. An automated analyzer comprising:

a main conveyance line capable of conveying a sample rack holding a sample;

a plurality of analysis units arranged along the main conveyance line;

a rack housing device housing the sample rack conveyed by the main conveyance line;

a sample processing area in which a sample held by a sample rack is subjected to a pipetting process, the sample processing area being provided for each analysis unit; and a controller controlling rack transferring operations so that when a first ordinary sample rack transferred from the rack supply device to the rack conveyance line needs to be received by a specific analysis unit and a second ordinary sample rack transferred from the rack supplying device to the main conveyance line subsequently to the first ordinary sample rack does not need to be received by the specific analysis unit, the second ordinary sample rack bypasses the specific analysis unit to be transferred towards the rack housing device while the first sample rack is received by the specific analysis unit, and when a calibrator sample rack holding a calibrator sample is received by any one of the plurality of analysis units, an ordinary sample rack transferred from the rack supply device to the rack conveyance line subsequently to the calibrator sample rack is prevented from bypassing the analysis unit by which the calibrator sample rack is received.

4. The automated analyzer according to claim 3, wherein the controller controlling rack transferring operations so that when an ordinary sample rack transferred from the rack supply device to the main conveyance line in advance of the calibrator sample rack does not finish being transferred, the calibrator sample rack is housed by the rack housing device after the preceding ordinary sample is housed thereby.

5. An automated analyzer comprising:

a main conveyance line capable of conveying a sample rack holding a sample;

a plurality of analysis units arranged along the main conveyance line;

a rack housing device housing the sample rack conveyed by the main conveyance line;

a sample processing area in which a sample held by a sample rack is subjected to a pipetting process, the sample processing area being provided for each analysis unit; and a controller controlling rack transferring operations so that when a first ordinary sample rack transferred from the rack supply device to the rack conveyance line needs to be received by a specific analysis unit and a second ordinary sample rack transferred from the rack supplying device to the main conveyance line subsequently to the first ordinary sample rack does not need to be received by the specific analysis unit, the second ordinary sample rack bypasses the specific analysis unit to be transferred towards the rack housing device while the first sample rack is received by the specific analysis unit, and when a control sample rack holding a control sample is received by any one of the plurality of analysis units, an ordinary sample rack transferred from the rack supply device to the rack conveyance line subsequently to the control sample rack is prevented from bypassing the analysis unit by which the control sample rack is received.

6. The automated analyzer according to claim 5, wherein the controller controlling rack transferring operations so that when an ordinary sample rack transferred from the rack supply device to the main conveyance line in advance of the control sample rack does not finish being transferred, the control sample rack is housed by the rack housing device after the preceding ordinary sample is housed thereby.

7. A method of conveying a sample rack supplied from a rack supply device through a main conveyance line to at least one of a plurality of analysis units, causing the sample rack to be subjected to a pipetting process for a sample held thereby, in the analysis unit to which the sample rack is conveyed, and conveying the sample rack subjected to the pipetting process to a rack housing device through the main conveyance device, the method comprising:

(1) controlling transferring operations of ordinary sample racks so that when a first ordinary sample rack which starts to be transferred by the main conveyance line needs to be received by a specific analysis unit and a second ordinary sample rack which starts to be transferred by the main conveyance line after the first ordinary sample rack starts to be transferred thereby does not need to be received by the specific analysis unit, the second ordinary sample rack bypasses the specific analysis unit to be transferred towards the rack housing device while the first sample rack is received by the specific analysis unit, and (2) controlling transferring operations of calibration sample racks and ordinary sample racks so that when an ordinary sample rack starts to be transferred by the main conveyance line after a calibration sample rack holding a calibration sample starts to be transferred thereby, the following ordinary sample rack is housed by the rack housing device after the preceding calibration sample rack is housed thereby.

8. The method according to claim 7, which further comprises controlling transferring operations of the calibration sample racks and ordinary sample racks so that when there is another ordinary sample rack to be transferred by the main conveyance line in advance of the calibration sample rack, the calibration sample rack is housed by the rack housing device after another ordinary sample rack mentioned above is housed thereby.

* * * * *